United States Patent [19]

Vanesky et al.

[11] Patent Number: 5,335,464
[45] Date of Patent: Aug. 9, 1994

[54] MAGNETICALLY SHIELDED ROOM WITH SLIDING DOOR

[75] Inventors: Frank W. Vanesky, Vista; Chris A. Isaacson, Poway; Bert M. Christie, Alta Loma, all of Calif.

[73] Assignee: Biomagnetic Technologies, Inc., San Diego, Calif.

[21] Appl. No.: 792,283

[22] Filed: Nov. 14, 1991

[51] Int. Cl.$^5$ ............................................. H05K 9/00
[52] U.S. Cl. ..................................... 52/173.1; 52/207; 49/477; 174/35 MS
[58] Field of Search ................... 52/173, 207, 173 OS, 52/173.1, 173.2, 207; 49/374, 378, 477, 478, 485; 174/35 MS

[56] References Cited

U.S. PATENT DOCUMENTS

| | | |
|---|---|---|
| 3,013,103 | 12/1961 | Pettler et al. . |
| 3,256,384 | 6/1966 | Lindgren .................... 174/35 MS |
| 3,364,298 | 1/1968 | Peters ........................ 174/35 MS |
| 3,507,974 | 4/1970 | Clark et al. .................... 49/477 |
| 3,518,355 | 6/1970 | Luce .......................... 174/35 MS |
| 3,531,577 | 9/1970 | Garlington ................ 174/35 MS |
| 3,557,777 | 1/1971 | Cohen . |
| 3,608,280 | 3/1972 | Martin . |
| 3,745,226 | 7/1973 | Nichols et al. . |
| 3,790,696 | 2/1974 | Lindgren . |
| 4,150,509 | 4/1979 | Knap ........................... 49/477 X |
| 4,177,353 | 12/1979 | McCormack .................. 49/477 X |
| 4,370,831 | 2/1983 | Hamilton ......................... 49/477 |
| 4,490,675 | 12/1984 | Knuettel et al. . |
| 4,651,099 | 3/1987 | Vinegar et al. . |
| 4,677,251 | 6/1987 | Merewether . |
| 4,755,630 | 7/1988 | Smith et al. . |
| 4,959,504 | 9/1990 | Yarger et al. . |
| 5,017,736 | 5/1991 | Yarger et al. ............ 174/35 MS |
| 5,081,071 | 1/1992 | Hirschkoff . |

OTHER PUBLICATIONS

Brochure entitled "Magnetic Shielded Rooms" by Falls Permalloy Rooms and Machine Shop. Date unknown.

*Primary Examiner*—Carl D. Friedman
*Assistant Examiner*—Robert J. Canfield
*Attorney, Agent, or Firm*—Gregory Garmong

[57] ABSTRACT

A magnetically shielded room has four walls, a floor, and a ceiling. One of the walls has a doorway therethrough, and a sliding door is provided to close the doorway. Each of the four walls, the floor, the ceiling, and the door is formed of at least one layer of electrically conductive material to exclude radio frequency energy from the interior of the room, and at least one layer of high magnetic permeability material to exclude magnetic fields from the interior of the room. Preferably, at least the wall with the doorway therethrough and the door are formed of two electrically conductive plates and a layer of high magnetic permeability material on each of the plates, the electrically conductive plates of the wall being spaced sufficiently far apart that the sliding door slides into the space between the plates when the doorway is opened. In this preferred approach, the door is mechanically, electrically, and magnetically sealed to the doorway in the wall by inflating bladders in the door that force the electrically conductive plates of the door against the respective plates of the wall, and the high magnetic permeability layers of the door against the respective layers of the wall.

5 Claims, 4 Drawing Sheets

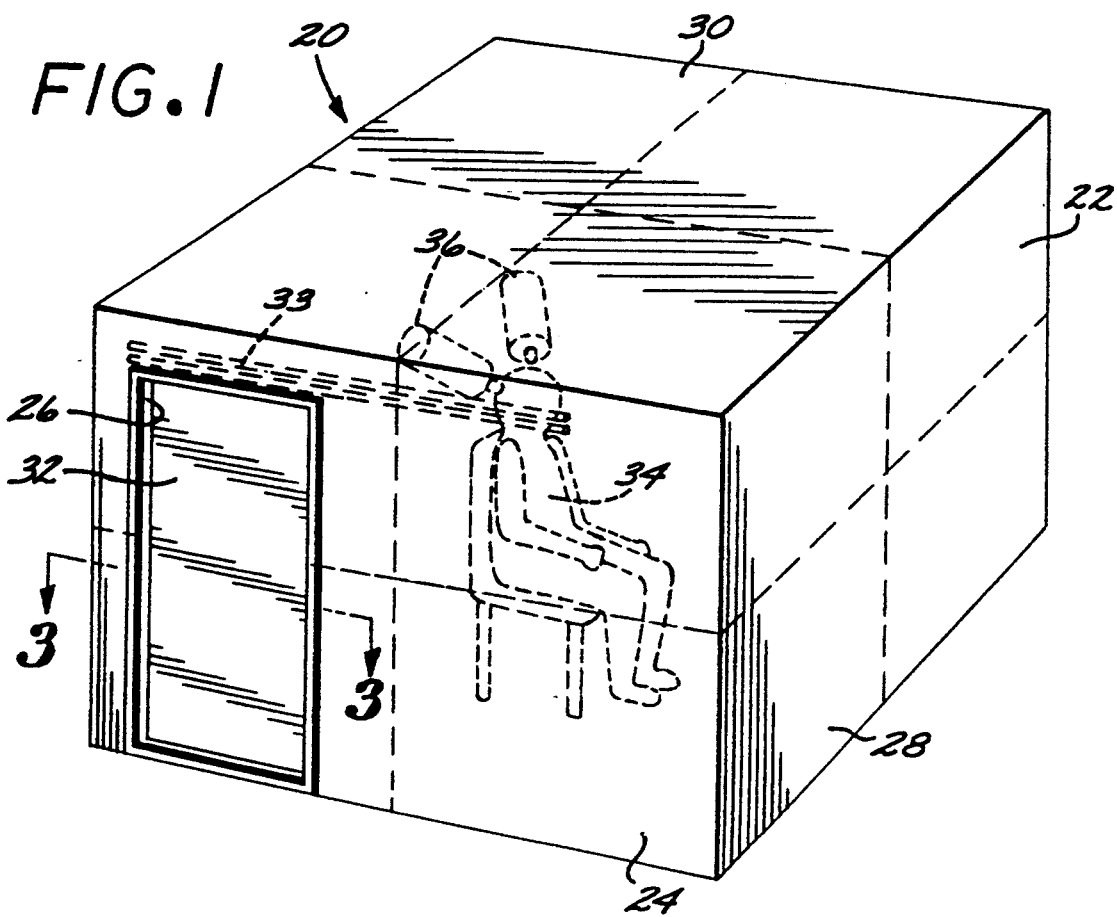
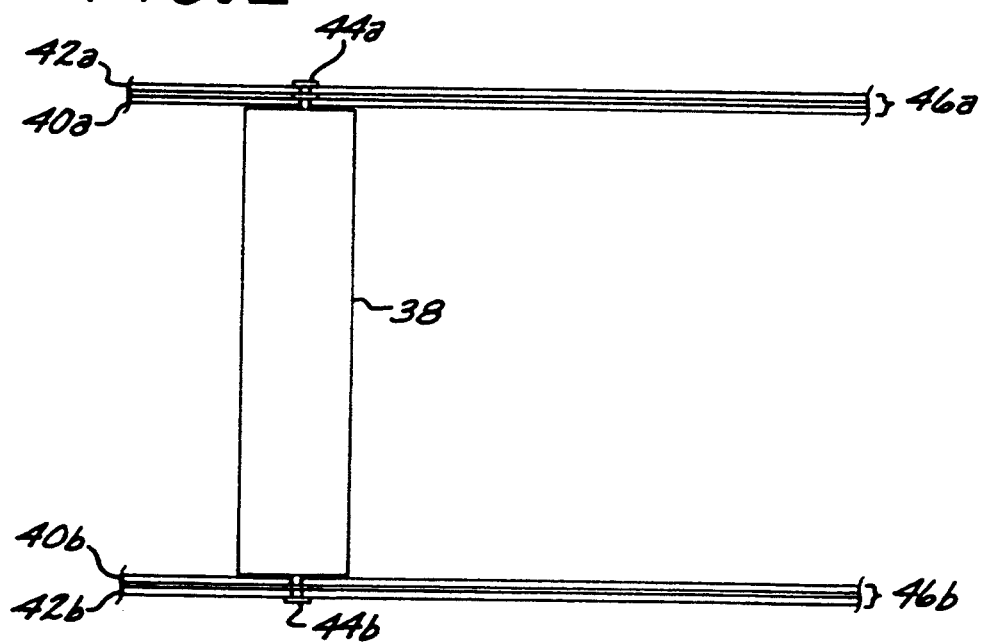

MAGNETICALLY SHIELDED ROOM WITH SLIDING DOOR

BACKGROUND OF THE INVENTION

This invention relates to magnetically shielded rooms, and, more particularly, to the construction of such a room having a sliding door for access to the room.

In biomagnetometry, magnetic fields produced by the human body are measured and studied both to diagnose ailments and to understand the functioning of the body. The magnetic fields of greatest interest are produced by the brain, and the strength of these fields produced by the brain are on the order of 1/10,000,000 of the strength of the magnetic field of the earth. There are several approaches to isolating the magnetic field of the brain from the ambient magnetic field of the earth and other sources. One approach is to provide sophisticated electronic filtering that separates the varying fields of the brain from the steady field of the earth. Such filtering electronics is expensive and not fully effective.

Another approach is to place the person whose magnetic field is under study into an isolating enclosure which shields the person and the magnetic field detector from external electromagnetic and magnetic fields, so that the biomagnetic field produced by the person constitutes a greater fraction of the total field within the enclosure. Such an enclosure is known in the art as a "magnetically shielded room" or MSR. The use of a magnetically shielded room in conjunction with some lesser level of electronic filtering than used in the absence of the MSR produces the best results for measurements of biomagnetic signals obtained to date.

One of the earliest magnetically shielded rooms is disclosed in U.S. Pat. No. 3,557,777. Although the configurations of the patented design and those of current commercial products vary somewhat and employ various modifications to improve performance and ease of construction, the basic design of a magnetically shielded room remains unchanged. Such a room includes four walls, a floor, a ceiling, and a door in one of the walls. This enclosure is structured to have a "continuous" electrically conductive layer that excludes radio frequency fields from the interior, and a "continuous" layer of a high magnetic permeability material that excludes magnetic fields from the interior of the MSR.

In this description, the word "continuous" is highlighted, because the layers cannot be truly continuous due to the need to construct the enclosure from sheets of finite size, because there are electrical feedthroughs to permit monitoring of the instrumentation in the room, and because there is a door in the enclosure to permit access to the interior of the MSR. Even tiny separations between sections of the layers can permit external fields to leak into the interior of the MSR. Many of the design improvements made to MSRs are aimed at removing field leakage paths while retaining reasonable weight, cost, and ease of construction of the MSR. In one approach, an additional layer of the high magnetic permeability material is added within the structure with its seams offset from those of the outer layer, in the hope of minimizing magnetic field leakage.

To date, magnetically shielded rooms have been made with swinging doors that seal to the facing wall in the manner of a refrigerator or cold-storage locker. This type of door provides moderately good sealing of the electrically conductive and high magnetic permeability layers, when there is one layer of each type, although it is difficult to attain good sealing at the bottom of the door along the threshhold of the doorway. When there is one electrically conductive layer and two layers of the high magnetic permeability material, it is more difficult to attain simultaneous sealing of all of the layers. There has been presented no good design for a swinging door when a second layer of the electrically conductive material is added, for a total of four layers.

Swinging doors are heavy, and may weigh from 800 to 1000 pounds, depending upon the details of construction. Swinging doors are cumbersome to use, requiring a larger "footprint" for the MSR than is required by the plan view of the room itself. Since the MSR is usually constructed within a room of a hospital or laboratory building, with the electronic and analytical support equipment in that exterior room, the operations can be quite cramped because of the space that must be allotted to the opening of the door. Swinging doors can pose some safety hazards in operation, particularly in a cramped environment.

There is therefore a need for a better approach to entry into a magnetically shielded room. Such an approach must permit excellent sealing of the shielding layers to exclude external fields, and desirably would be more convenient to use than the existing approach. The present invention fulfills this need, and further provides related advantages.

SUMMARY OF THE INVENTION

The present invention provides a magnetically shielded room having multiple layers of radio frequency and magnetic field shielding. The door of the room does not require maintaining a large clear area to permit opening of the door, and does not have the safety concerns inherent with swinging doors. The MSR has excellent sealing against leakage of electromagnetic and magnetic fields when the door is closed and sealed.

In accordance with the invention, a magnetically shielded room comprises four walls, a ceiling, and a floor, each of the walls, ceiling, and floor having at least one layer of a high magnetic permeability material and at least one layer of an electrically conductive material. One of the walls has a doorway therethrough. A sliding door slides parallel to the wall having the doorway therethrough, the sliding door moving from a first position wherein the door covers the doorway to a second position wherein the door does not cover the doorway. The door has at least one layer of a high magnetic permeability material and at least one layer of an electrically conductive material. Means for sealing seals the sliding door against the wall having the doorway therethrough when the sliding door is in the first position. The means for sealing achieves a seal of a layer of high magnetic permeability material of the door to a layer of high magnetic permeability material of the wall, and achieves a seal of a layer of electrically conductive material of the door to a layer of electrically conductive material of the wall.

The magnetically shielded room of the invention utilizes a sliding door to close the access doorway, rather than a hinged swinging door. The sliding door has the same types of layered structure as the stationary wall, and achieves seals to the respective layers of the wall to exclude radio frequency and magnetic fields from the interior of the MSR.

More specifically, a magnetically shielded room comprises three walls, a ceiling, and a floor, each of the three walls, ceiling, and floor having at least one layer of a high magnetic permeability material and at least one layer of an electrically conductive material, and a fourth wall having a doorway therethrough. The fourth wall has an outer wall segment and an inner wall segment inwardly spaced from the outer wall segment, at least one of the wall segments having a layer of a high magnetic permeability material and a layer of an electrically conductive material. A sliding door is disposed between the two wall segments of the fourth wall and is supported to slide parallel to the fourth wall from a first position wherein the door covers the doorway to a second position wherein the door does not cover the doorway. The door has a layer of a high magnetic permeability material and a layer of an electrically conductive material. A means for sealing seals the sliding door against the fourth wall. The means for sealing achieves a seal of the layer of high magnetic permeability material of the door to the layer of high magnetic permeability material of the fourth wall, and achieves a seal of the layer of electrically conductive material of the door to the layer of electrically conductive material of the fourth wall.

In one embodiment, both of the wall segments of the fourth wall have a layer of a high magnetic permeability material and a layer of an electrically conductive material. The door has two layers of high magnetic permeability material and two layers of electrically conductive material, with each of the layers of high magnetic permeability material of the door in facing relation with the layer of high magnetic permeability material of one of the wall segments and each of the layers of electrically conductive material of the door in facing relation with the layer of electrically conductive material of one of the wall segments. The means for sealing achieves a seal of each of the layers of high magnetic permeability material of the door to the facing layer of high magnetic permeability material of the wall, and a seal of each of the layers of electrically conductive material of the door to the facing layer of electrically conductive material of the wall. Preferably, the means for sealing includes a bladder that forces the facing layers of high magnetic permeability material and the facing layers of electrically conductive material into sealing contact with each other when the bladder is inflated. In this approach, the electrically conductive material of the walls and the door is aluminum alloy having tin, copper, or other high-conductivity material applied to the surfaces of the aluminum alloy that form the seals to the respective facing surfaces when the door is in the first position, and the high magnetic permeability material is mu-metal. Other types of seals may also be used, such as mechanical, electromechanical, or electro-pneumatic seals that are selectively movable between an open position where the seal does not force the facing layers into sealing contact and a closed position where the seal forces the facing layers into sealing contact when the door is in the first position.

A sliding door does not substantially increase the plan view area, or footprint, required for the magnetically shielded room above that of the area required for the room itself. A sliding door is safer than a swinging door, and can be made to achieve better sealing at four seals, two of each type, than a swinging door. Achieving a good seal with a swinging door is extremely difficult. Other features and advantages of the invention will be apparent from the following more detailed description of the preferred embodiment, taken in conjunction with the accompanying drawings, which illustrate, by way of example, the principles of the invention.

BRIEF DESCRIPTION OF THE DRAWINGS

FIG. 1 is a perspective cutaway view of a magnetically shielded room utilizing the approach of the invention;

FIG. 2 is an enlarged sectional view of the wall in which the door of the magnetically shielded room is placed, taken generally along line 2—2 of FIG. 1;

DETAILED DESCRIPTION OF THE PREFERRED EMBODIMENTS

Figure 3:
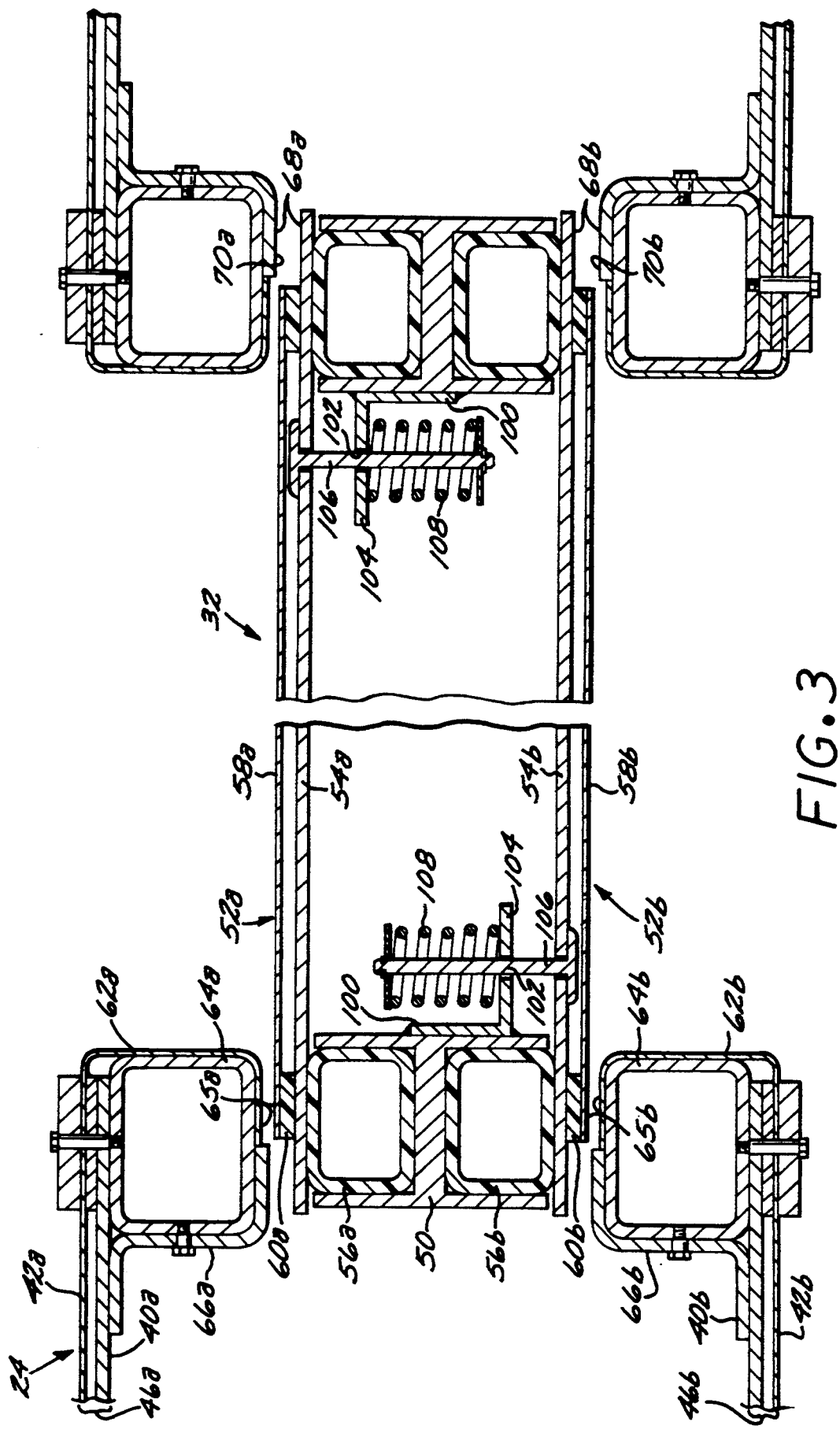
FIG. 3 is an enlarged sectional view of the sliding door to the magnetically shielded room and the adjacent portions of the wall, with the door in its unsealed condition, taken generally along line 3—3 of FIG. 1.

In accordance with a preferred embodiment of the invention, a magnetically shielded room comprises three walls, a ceiling, and a floor. Each of the three walls, ceiling, and floor has two layers of a high magnetic permeability material and two layers of an electrically conductive material. A fourth wall has a doorway therethrough. The fourth wall has an outer wall segment and an inner wall segment inwardly spaced from the outer wall segment. The outer wall segment comprises an electrically conductive metal plate and an outwardly facing layer of a high magnetic permeability material, and the inner wall segment comprises an electrically conductive metal plate and an inwardly facing layer of a high magnetic permeability material. A sliding door is disposed between the two wall segments of the fourth wall and is supported to slide parallel to the fourth wall from a first position wherein the door covers the doorway to a second position wherein the door does not cover the doorway. The door comprises an outer door segment and an inner door segment. The outer door segment comprises an outer electrically conductive metal plate and an outwardly facing layer of a high magnetic permeability material, and the inner door segment comprises an inner electrically conductive metal plate and an inwardly facing layer of a high magnetic permeability material. A pair of inflatable bladders seal the sliding door is in the first position. The pair of inflatable bladders include an outer bladder that forces the outer door segment outwardly to seal against the outer wall segment of the fourth wall, and an inner bladder that forces the inner door segment inwardly to seal against the inner wall segment of the fourth wall. The respective outer conductive metal plates and outwardly facing layers of high magnetic permeability material seal against each other, and the respective inner conductive metal plates and inwardly facing layers of high magnetic permeability material seal against each other.

FIG. 1 illustrates a magnetically shielded room (MSR) 20 having three walls 22 with no doorway therethrough, a fourth wall 24 with a doorway 26 therethrough, a floor 28, and a ceiling 30. A sliding door 32 slides on a track 33 from an illustrated first position whereat the door 32 covers the doorway 26, and a second position whereat the door 32 is moved laterally away from the doorway 26 so that the doorway is open. In a typical application, a person 34 is positioned inside the shielded room 20, with one or more biomagnetometer assemblies 36 positioned for making biomagnetic measurements of the person 34. By way of illustration of the dimensions but not of limitation, the height of the room 20 is typically about 8 feet.

FIG. 2 depicts the structure of the walls 22 and 24 (away from the doorway 26), the floor 28, and the ceiling 30. A frame made of beams 38 is constructed of a nonmagnetic material such as aluminum alloy or wood. To the beams 38 are fixed panels or plates 40 of an electrically conducting material. Overlying the electrically conducting plates 40 are plates 42 of a high magnetic permeability material. The plates 40 and 42 are attached to the beams 38 using nonmagnetic fasteners 44. Each pair of plates 40 and 42 forms a wall segment 46. The preferred MSR 20 thus utilizes two segments 46a and 46b throughout to minimize the penetration of radio frequency and magnetic fields into the MSR. (The suffix "a" is used herein to indicate an "outer" or outwardly facing element of structure, and the suffix "b" is used to indicate an "inner" or inwardly facing element of structure.) In the preferred practice, the outer segment 46a has the plate 42a facing outwardly and the inner segment 46b has the plate 42b facing inwardly.

The beams 38 and the electrically conductive plates 40 are preferably formed of an aluminum alloy such as 1100 or 6061 alloy, although the invention is not so limited. The electrically conductive structure provides a shield against penetration of external electromagnetic fields into the room 20. The typical lateral dimensions of the plates are 4 feet by 10 feet. The plates 42 are made of a high magnetic permeability material that prevents the penetration of external magnetic fields into the interior of the room 20. The preferred material of construction of the plates 42 is mu-metal, which has a composition of about 75 weight percent nickel, 5 weight percent copper, 2 weight percent chromium, balance iron, and is available commercially in plate form. Examples of other commercially available materials that can be used for the plates 42 are permalloy, having a composition of 78.5 weight percent nickel, 21.2 weight percent iron, 0.3 weight percent manganese, and supermalloy, having a composition of 79 weight percent nickel, 15.7 weight percent iron, 5 weight percent molybdenum, and 0.3 weight percent manganese.

Figure 4:
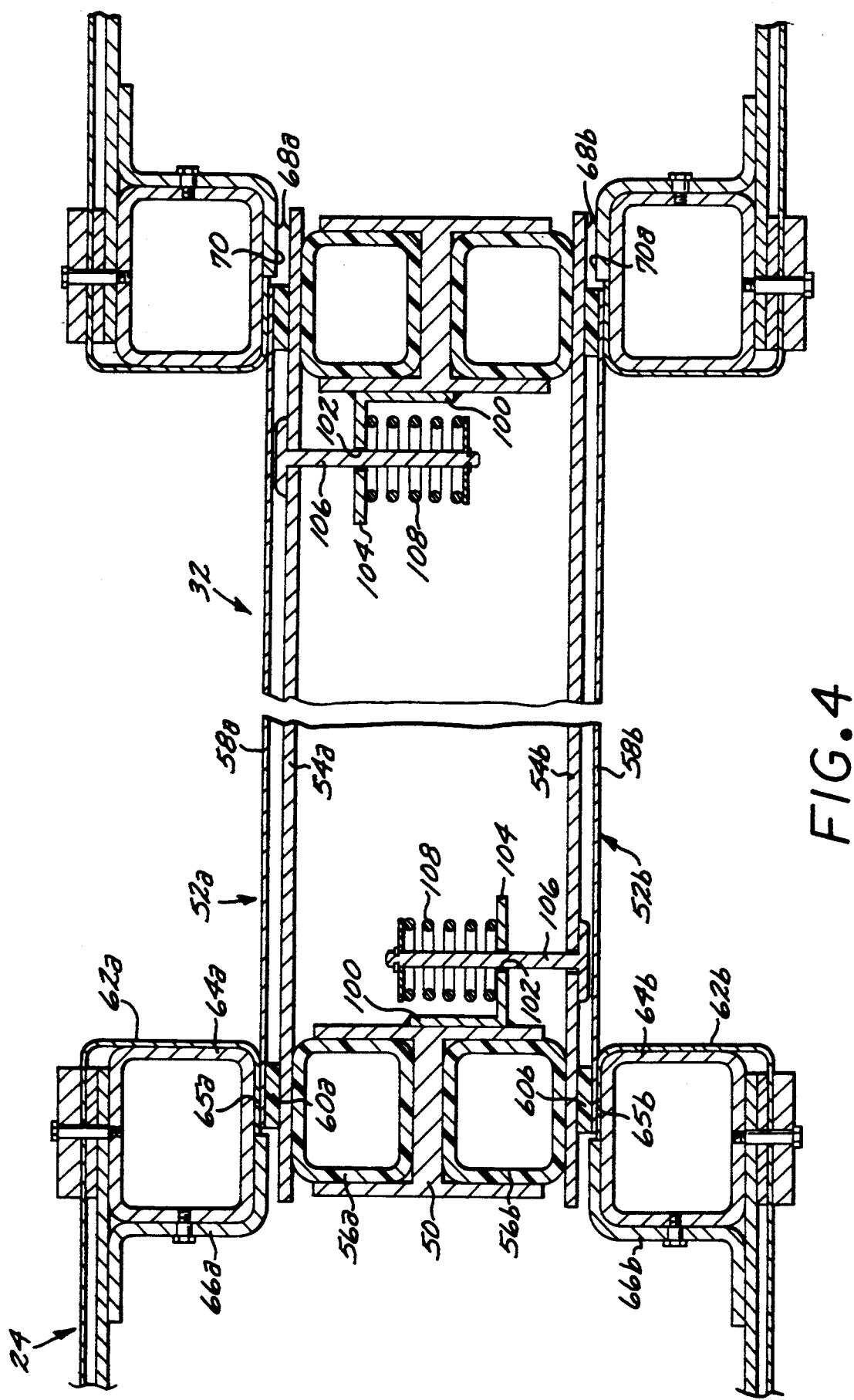
FIG. 4 is a sectional view of the door similar to that of FIG. 3, except with the door in the sealed condition.

FIGS. 3 and 4 depict the sliding door 32 and adjacent portions of the wall 24 in the unsealed and sealed conditions, respectively. The door 32 includes a central beam 50 made of an electrically conducting material. Supported on the beam 50 are an outer segment 52a and an inner segment 52b. Each segment 52a and 52b includes an electrically conductive plate 54a and 54b, respectively, mounted to the beam 50 by a structural element that permits the segments 52a and 52b to move outwardly and inwardly, respectively, in a controllable fashion. In the preferred approach, the segments 52 are mounted to the beam 50 using an L-shaped bracket 100 extending from the side of the beam 50. A bore 102 extends through a leg 104 of the bracket 100 which is not attached to the beam 50, and faces the segments 52. A shaft 106 passes through the bore 102, and is fastened to the plate 54 portion of the segment 52. A spring 108 extends between the end of the shaft 106 remote from the segment 52, and the leg 104 of the bracket 100.

(FIGS. 3 and 4 depict exemplary outer and inner support structures, but it will be appreciated that similar outer and inner support structures are distributed around the periphery of the door.) The springs 108 force the segments 52 to lie flat against the support beams 50 to allow the door to slide between the first and second (closed and open) positions.

In the preferred approach, an inflatable bladder 56 is positioned between and reacts between the beam 50, which serves as a reaction member that is spaced apart from the wall 24, and the plate 54, forcing the plate 54 (and segment 52) away from the beam 50 when a seal is to be made. The bladder approach is preferred, because no mechanism need be mounted to the door. Only a pressurization line is required, and the pressurization apparatus may be remotely placed outside the MSR 20. Equivalently, any operable type of pneumatic, mechanical, electromechanical, or electrical device may be used to effect the sealing action, but if a mechanism is mounted on the door, it must be adequately shielded.

A plate 58a or 58b of a high magnetic permeability material is mounted to the respective electrically conductive plate 54a or 54b by a compliant support 60. The plates 58 are smaller in lateral extent that the plates 54, to provide sealing surfaces as will be described. The electrically conductive plates 54 are preferably made of an aluminum alloy, the high magnetic permeability plates 58 are preferably made of mu-metal, permalloy, or supermalloy, and the compliant support 60 is preferably made of foam or rubber.

The wall 24 is formed of segments 46, as discussed previously. Each segment 46 ends in a door frame 62, the door frames 62 collectively forming the doorway 26. The high magnetic permeability plate of each segment 46 is formed around the door frame 62 as an extension 64 that lies against the side of the door frame 62 that faces the door 32. The extension 64 of the high magnetic permeability material thus is in a facing relation along a facing surface 65 to the end of the respective high magnetic permeability plate 58 of the door 32.

A generally Z-shaped bracket extension 66 attaches to the door frame 62. One leg of the extension 66 attaches to the surface of the plate 40 and the other lies against the side of the door frame 62 that faces the door 32 in a facing relation to the plate 40 of the door 32. The bracket extension 66 is formed of an electrically conductive material such as the same aluminum alloy that forms the plate 54. One, or preferably both, of the facing surfaces 68 of the bracket extension 66 and the plate 54 is coated with a layer of a highly conductive metal 70, which is preferably copper, tin, or zinc. When pressed together, the layers of conductive metal 70 permit a positive electrically conducting seal along the facing surfaces 68, thereby forming a continuous electrically conducting path from the plate 40 to the plate 54, through the extension 66. A pressed aluminum-to-aluminum contact is not preferred for forming the electrically conducting path, because of the aluminum oxide resistive barrier at the interface.

In FIG. 3, the bladders 56 are not inflated, and there is a separation on each side between the door 32 and the frame 62. The door 32 is dimensioned so that it slides into the space between the segments 46 of the wall 24 and between the door frame members 62 along the track 33, to open the doorway 26.

In FIG. 4, the bladders 56 are shown as inflated, forcing the facing surfaces 65 together to seal the doorway against leakage of magnetic fields into the interior of the room 20, and forcing the facing surfaces 68 together to seal the doorway against leakage of electromagnetic fields such as radio frequency fields into the interior of the room 20. The inflated bladders 56 place pressure directly upon the facing surfaces 68. As the plate 54 is forced outwardly by the inflated bladders 56, the plate 58 is also forced toward the extension 64. The compliant support 60 adjusts the position of the plate 54 to a good sealing contact to the extension 64. The frictional contacts along the facing surfaces 65 and 68 also provide a mechanical seal around the edges of the sliding door 32, so that it is firmly held in the closed or first position as shown in FIG. 4. When the door is to be opened by sliding it out of the doorway, the bladders 56 are deflated to the state shown in FIG. 3.

The present approach provides excellent sealing of the doorway by the sliding door. A prototype shielded room with a sliding door was fabricated in accordance with the preferred embodiment just described. This prototype was tested for shielding performance against electromagnetic fields with frequencies between 0.05 Hz (Hertz) and 25 Hz. Tests were conducted at a location near a wall of the shielded room without the sliding door, and also at a location directly in front of the sliding door. The shielding performance at the wall without the door was equal to or better than that of commercially available rooms. The shielding performance in front of the door was degraded from that measured at the wall without the door by less than a factor of two at all frequencies tested. This performance is well within the requirements for most practical applications. In the case of biomagnetometers, for example, the shielding performance measured would be satisfactory for all hospital environments in which such biomagnetometers have been installed to date.

Figure 5:
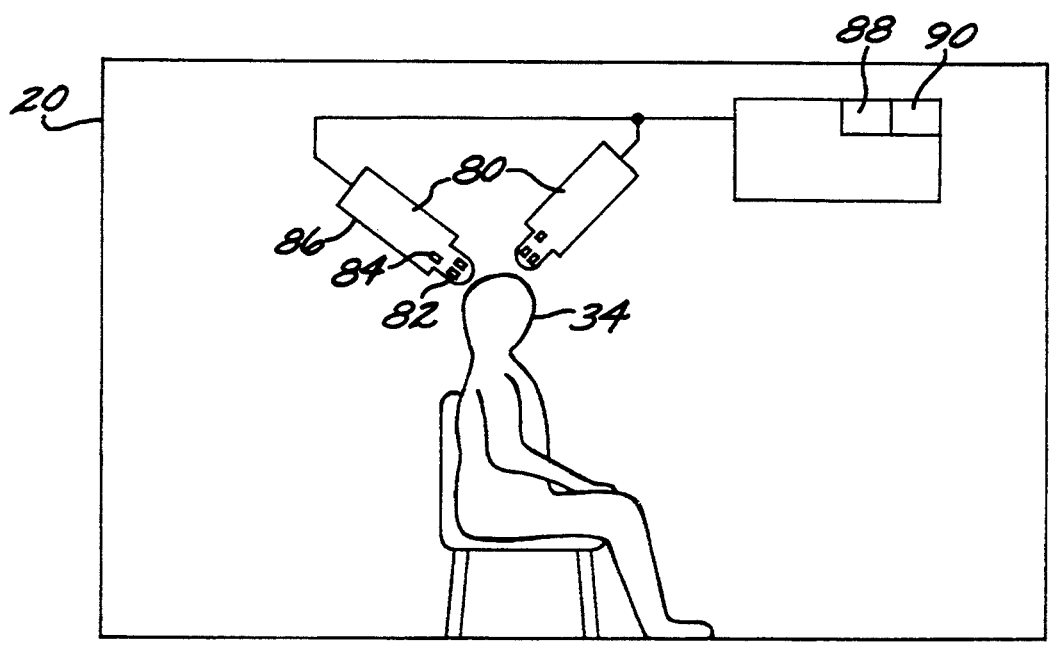
FIG. 5 is a schematic depiction of the operation of the biomagnetometer within the magnetically shielded room.

In the preferred approach, the magnetically shielded room of the invention is preferably used in conjunction with biomagnetic measurements as shown in FIGS. 1 and 5. Referring to FIG. 5, a biomagnetometer 80 includes a plurality of magnetic sensing coils 82 for measuring small magnetic fields. The output signal of each magnetic sensing coil 82 is detected by a detector, preferably a superconducting quantum interference device (SQUID) 84. Both the magnetic sensing coil 82 and the SQUID 84 are maintained at a cryogenic operating temperature within a liquid helium dewar 86.

The magnetic signals from the body of the person 34 are picked up by the magnetic sensing coils 82 in the dewar 86, and the signals are detected by the SQUIDs 84. The SQUIDs detect the magnetic field as electrical currents that are processed in an electronics system 88 and stored in a computer 90 as a function of time, for display and study.

The general structure of biomagnetometers 80, including the magnetic sensing coils 82, the SQUIDs 84, the dewars 86, the electronics 88, and the computer 90 are known in the art. See for example, U.S. Pat. Nos. 4,793,355; 3,980,076; 4,389,612; 4,079,730; 4,386,361; and 4,403,189, whose disclosures are incorporated by reference.

Although particular embodiments of the invention have been described in detail for purposes of illustration, various modifications may be made without departing from the spirit and scope of the invention. Accordingly, the invention is not to be limited except as by the appended claims.

What is claimed is:

1. A magnetically shielded room, comprising:

three walls, a ceiling, and a floor, each of the three walls, ceiling, and floor having two layers of a high magnetic permeability material and two layers of an electrically conductive material;

a fourth wall having a doorway therethrough, the fourth wall having an outer wall segment and an inner wall segment inwardly spaced from the outer wall segment, the outer wall segment comprising an electrically conductive metal plate and an outwardly facing layer of a high magnetic permeability material, and the inner wall segment comprising an electrically conductive metal plate and an inwardly facing layer of a high magnetic permeability material;

a sliding door that is disposed between the two wall segments of the fourth wall and is supported to slide parallel to the fourth wall from a first position wherein the door covers the doorway to a second position wherein the door does not cover the doorway, the door comprising an outer door segment and an inner door segment, the outer door segment comprising an outer electrically conductive metal plate and an outwardly facing layer of a high magnetic permeability material, and the inner door segment comprising an inner electrically conductive metal plate and an inwardly facing layer of a high magnetic permeability material; and a pair of inflatable bladders that seal the sliding door against the fourth wall when the sliding door is in the first position, the pair of inflatable bladders including an outer bladder that forces the outer door segment outwardly to seal against the outer wall segment of the fourth wall, and an inner bladder that forces the inner door segment inwardly to seal against the inner wall segment of the fourth wall such that the respective outer conductive metal plates and outwardly facing layers of high magnetic permeability material seal against each other, and the respective inner conductive metal plates and inwardly facing layers of high magnetic permeability material seal against each other.

2. The magnetically shielded room of claim 1, wherein each of the wall segments of the fourth wall includes a door frame defining the doorway, the door frame having the electrically conductive metal plate supported thereon and the layer of high magnetic permeability material supported on the electrically conductive metal plate, and further wherein the electrically conductive metal plate of the outer wall segment includes a sealing extension that lies on an inwardly facing surface of the supporting door frame and wherein the layer of high magnetic permeability material of the outer wall segment includes a sealing extension that lies on the inwardly facing surface of the door frame which supports the outer wall segment, and further wherein the electrically conductive metal plate of the inner wall segment includes a sealing extension that lies on an outwardly facing surface of the supporting door frame and wherein the layer of high magnetic permeability material of the inner wall segment includes a sealing extension that lies on the outwardly facing surface of the door frame which supports the inner wall segment.

3. The magnetically shielded room of claim 1, wherein the outwardly facing layer of high magnetic permeability material of the door is resiliently mounted to the outer electrically conductive plate of the door, and the inwardly facing layer of high magnetic permeability material of the door is resiliently mounted to the inner electrically conductive plate of the door.

4. The magnetically shielded room of claim 3, wherein the outer electrically conductive plate of the door is mounted to the outer bladder, and the inner electrically conductive plate of the door is mounted to the inner bladder.

5. The magnetically shielded room of claim 1, wherein the electrically conductive plates of the fourth wall and the door are aluminum alloy having an electrically conductive coating applied to the surfaces of the aluminum alloy that form the seals to the respective facing surfaces when the door is in the first position.

* * * * *